US010194815B2

(12) United States Patent
Herleikson

(10) Patent No.: US 10,194,815 B2
(45) **Date of Patent: *Feb. 5, 2019**

(54) VARIABLE BANDWIDTH ECG HIGH PASS FILTER

(71) Applicant: KONINKLIJKE PHILIPS N.V., Eindhoven (NL)

(72) Inventor: Earl Clark Herleikson, Cinebar, WA (US)

(73) Assignee: Koninklijke Philips N.V., Eindhoven (NL)

( * ) Notice: Subject to any disclaimer, the term of this patent is extended or adjusted under 35 U.S.C. 154(b) by 200 days.

This patent is subject to a terminal disclaimer.

(21) Appl. No.: 15/034,428

(22) PCT Filed: Oct. 10, 2014

(86) PCT No.: PCT/IB2014/065206

§ 371 (c)(1),
(2) Date: May 4, 2016

(87) PCT Pub. No.: WO2015/068066

PCT Pub. Date: May 14, 2015

(65) Prior Publication Data

US 2016/0262645 A1 Sep. 15, 2016

Related U.S. Application Data

(60) Provisional application No. 61/901,491, filed on Nov. 8, 2013.

(51) Int. Cl.

*A61B 5/04* (2006.01)
*A61B 5/00* (2006.01)

(Continued)

(52) U.S. Cl.

CPC ........ *A61B 5/04017* (2013.01); *A61B 5/0428* (2013.01); *A61B 5/725* (2013.01); *A61N 1/3925* (2013.01); *A61N 1/3987* (2013.01)

(58) Field of Classification Search

CPC ............................ A61B 5/04017; A61B 5/725
See application file for complete search history.

(56) References Cited

U.S. PATENT DOCUMENTS 4,472,785 A * 9/1984 Kasuga .............. H03H 17/0685 327/113
5,269,313 A 12/1993 Depinto (Continued)

FOREIGN PATENT DOCUMENTS

CN 103379860 A 10/2013
EP 0634135 B1 4/1997

(Continued)

OTHER PUBLICATIONS

Sornmo, Leif "Institute of Electrical and Electronics Engineers: Time Varying Filtering for Removal of Baseline Wander in Exercise ECGs", Proceedings of the Computers in Cardiology Meetings, vol. Meeting 18, 1991.

(Continued)

*Primary Examiner* — William J Levicky

(57) ABSTRACT

An electrocardiogram high pass filter (25) employs a baseline low pass filter (40), a signal delay (44) and a signal extractor (45). In operation, baseline low pass filter (40) includes a finite impulse response filter (41) and an infinite impulse response low pass filter (42) cooperatively low pass filtering a baseline unfiltered electrocardiogram signal (ECGbu) to output a filtered baseline signal (BSEf). Baseline low pass filter (40) further includes a baseline wander estimator (43) dynamically adjusting a corner frequency of baseline low pass filter (40) as a function of an estimation of any baseline wander within the baseline unfiltered electro- (Continued)

ECG monitor 23
Signal processor 24
VB ECG HP filter 25 (FIGS. 2-6)
ECG display 26
30a 30b
28a 28b
Defibrillation controller 27
31a
Shock source 29
32a 32b
20 10 11 22 21a 21b cardiogram signal (ECGbu). Signal delay (44) time delays the baseline unfiltered electrocardiogram signal (ECGbu) to output a delayed baseline unfiltered electrocardiogram signal (ECGdbu), and signal extractor (45) extracts the filtered baseline signal (BSEf) from the delayed baseline unfiltered electrocardiogram signal (ECGdbu) to output a baseline filtered electrocardiogram signal (ECGbf).

15 Claims, 9 Drawing Sheets

(51) Int. Cl.
*A61N 1/39* (2006.01)
*A61B 5/0428* (2006.01)

(56) References Cited

U.S. PATENT DOCUMENTS 5,357,969 A * 10/1994 Herleikson .......... A61B 5/0428 600/508
5,433,208 A * 7/1995 Lundstrom ........ A61B 5/04017 600/508
6,041,250 A 3/2000 Depinto
6,280,391 B1 8/2001 Olson et al.
2007/0078354 A1 4/2007 Holland

FOREIGN PATENT DOCUMENTS

| | | | |
|---|---|---|---|
| JP | H06504696 | A | 6/1994 |
| JP | 2009509711 | A | 3/2009 |
| WO | 2007044125 | A1 | 4/2007 |
| WO | 2011135646 | A1 | 7/2013 |

OTHER PUBLICATIONS

Sornmo, Leif et al "Biolectrical Signal Processing in Cardiac and Neurological Applications", National Center for Biotechnology Information, 2007.
Depinto et al "Filters for the Reduction of Baseline Wander and Muscle Artifact in the ECG" Journal of Electrocardiology, vol. 5, Jan. 1992, pp. 40-48.
Holly, Benedikt et al "Digital Filtration of Artifacts in ECG", Digital Processing of Audio, Video and Biomedical Signals, 2004.
Haing, Aung Soe et al "Quantitative Investigation of Digital Filters in Electrocardiogram with Simulated Noises", International Journal of Information and Electronics Engineering, vol. 1, No. 3, Nov. 2011.

* cited by examiner

VARIABLE BANDWIDTH ECG HIGH PASS FILTER

This application is a national stage application under 35 U.S.C. § 371 of International Application No. PCT/IB2014/065206 filed on Oct. 10, 2014 and published in the English language on May 14, 2015 as International Publication No. WO/2015/068066, which claims priority to U.S. Application No. 61/901,491 filed on Nov. 8, 2013, the entire disclosures of which are incorporated herein by reference.

FIELD OF THE INVENTION

The present invention generally relates to high pass filtering of electrocardiogram ("ECG") signals. The present invention specifically relates to a variable bandwidth high pass filtering of ECG signals for diagnostic and emergency medical service ("EMS") purposes.

BACKGROUND OF THE INVENTION

As known in the art, a signal amplitude of ECG signals is typically in the order of 1 mV, but may have a DC offset that varies from as much as −300 mV to +300 mV. This DC offset may drift with time and/or patient movement, and is often referred to as a "baseline wander". Additionally, events such as defibrillation may have a dramatic effect on the baseline. In particular, a DC offset following a defibrillation event is usually drifting due to current that may flow through the ECG electrodes during the defibrillation event.

A typical ECG signal display setting for gain has a range of +/−2 mV in order to visually see a 1 mV ECG signal clearly. In response to potentially large and drifting DC offsets, high pass filters have been utilized to remove any DC offset in order to keep the ECG signal within view windows of a display and a printer. More particularly, a key diagnostic measurement of a ECG signal is the ST segment elevation or depression. This is performed by comparing a baseline of the ECG signal prior to a QRS with the baseline after the QRS. Ideally, the high pass filter should remove the baseline wander in such a way that the relative level of the baseline before and after the QRS is not affected.

ECG standards have been established that describe an impulse response requirement for diagnostic quality ECG measurements (e.g., EN 60601-2-27 and AAMI EC13). For example, an impulse applied in a standard test is 3 mV in amplitude with a duration of 100 mS, and the requirement is that a baseline should be displaced by less than 100 uV and a slope of the baseline should be less than 300 uV/sec following the impulse. Therefore, a high pass filter in an ECG system has conflicting goals.

Specifically, if the high pass filter is very responsive to the baseline wander in order to reliably maintain the baseline of the ECG signal in the center of the display, then it will also likely be responsive to the QRS such that the baseline following the QRS is displaced following the QRS by more than 100 uV. This is why an ECG monitor usually provides the clinician with several bandwidth settings for the high pass filter. The settings are often referred to as "Monitor" bandwidth for keeping the ECG signal visible on the display screen, and as "Diagnostic" bandwidth for making diagnostic ECG measurements (e.g., ST segment elevation and depression). Additionally, there is also the desire to display the ECG signal in real time with minimal time delay. This is important for clinical applications where timing is important such as synchronized cardioversion.

Historically, several types of high pass filters have been utilized in ECG monitors.

One such type of high pass filter for ECG monitors is an infinite impulse response ("IIR") high pass filter that is computationally simple to implement. For example, a second order Butterworth high pass filter is easily implemented with five (5) multiply and accumulate calculations per sample with minimal time delay. However, a disadvantage of a BR high pass filter is that a group delay is frequency dependent. This results in distortion of the ECG signal. Stated in another way, a BR high pass filter responds to a positive ECG QRS signal by depressing the baseline following the ECG signal. Furthermore, in order to minimize the distortion to a level acceptable for diagnostic purposes, the corner frequency of the IIR high pass filter needs to be reduced to a frequency of 0.05 Hz or less. Additionally, a first order IIR high pass filter applied to a ramp will result in a DC offset and a second order IIR high pass filter applied to a ramp will result in a zero (0) DC offset. Thus, in order to remove a DC offset that is drifting following a defibrillation event, the IIR high pass filter would need to be at minimum a second order filter.

Another type of high pass filter for ECG monitors is a finite impulse response ("FIR") high pass filter, which by definition has linear phase and constant group delay. Of note, a FIR high pass filter minimizes the distortion of the ECG signal due to the constant group delay and a 0.5 Hz or even a 0.67 Hz FIR high pass filter maybe implemented that meet the requirements for diagnostic quality ECG measurements in accordance ECG standards. Also, a FIR high pass filter responds well to a drifting DC offset following defibrillation, because it is usually designed to be symmetrical and an application of a FIR high pass filter to a ramp will produce a zero (0) DC offset. However, there are a couple of disadvantages of the FIR high pass filter. The first disadvantage is the time delay. Specifically, in order to have constant time delay for all frequencies, both the frequencies above and below the high pass corner frequency will see the same time delay, and a typical time delay is on the order of about one (1) second. The second disadvantage is the computational effort required. Specifically, a FIR high pass filter with one (1) second of time delay will have two (2) seconds of time history. A sample rate of 1000 Hz would require 2000 multiply accumulate calculations for each sample calculated at the 1000 Hz sample rate. Thus, for a full twelve (12) lead measurement, the number of multiply accumulate operations is 24M just for the FIR high pass filter.

Moreover, ECG monitoring is often performed on patients that are being moved. The out of hospital emergency medical services ("EMS") typically see significant baseline wander of the ECG due to the movement of the patient. An EMS High pass filter is often provided for ECG systems designed for the EMS environment. This high pass filter will typically have a corner frequency in the range of 1 Hz to 2 Hz. A simple IIR filter with this high a corner frequency very substantially distorts the ECG waveform. A FIR filter with this corner frequency will minimize distortion of the ECG but would require a significant increase in computational effort.

SUMMARY OF THE INVENTION

To address the disadvantages of the prior art, the present invention provides a variable ECG high pass filter for diagnostic purposes (e.g., a corner frequency of 0.67 Hz or less) and also for EMS purposes (e.g., a corner frequency in the range of 1 Hz to 2 Hz). One form of the ECG high pass filter employs a baseline low pass filter, a signal delay and a signal extractor. In operation, the baseline low pass filter includes a finite impulse response filter and an infinite impulse response low pass filter cooperatively low pass filtering a baseline unfiltered ECG signal to output a filtered baseline signal. The baseline low pass filter further includes a baseline estimator dynamically adjusting the corner frequency of the baseline low pass filter as a function of an estimation of any baseline wander within the baseline unfiltered ECG signal. The signal delay time delays the baseline unfiltered ECG signal to output a delayed baseline unfiltered ECG signal, and the signal extractor extracts the filtered baseline signal from the delayed baseline unfiltered ECG signal to output a baseline filtered ECG signal.

A second form of the present invention is a ECG monitor employing a signal processor to generate an ECG waveform of a heart of a patient and an ECG display to display the ECG waveform (e.g., visualized on a computer screen or in a printout). The signal processor incorporates the aforementioned ECG high pass filter of the present invention for diagnostic purposes and/or EMS purposes.

A third form of the present invention is a defibrillator, automatic or manual, employing an ECG monitor to generate an ECG waveform of a heart of a patient, a shock source to store shock energy and a defibrillation controller to control a delivery of the shock energy to the heart of the patient responsive to a QRS analysis of the electrocardiogram waveform. The ECG monitor incorporates the aforementioned ECG high pass filter of the present invention for diagnostic purposes and/or EMS purposes.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

To facilitate an understanding of the present invention, exemplary embodiments of the present invention will be provided herein directed to ECG high pass filter for a defibrillator.

Figure 1:
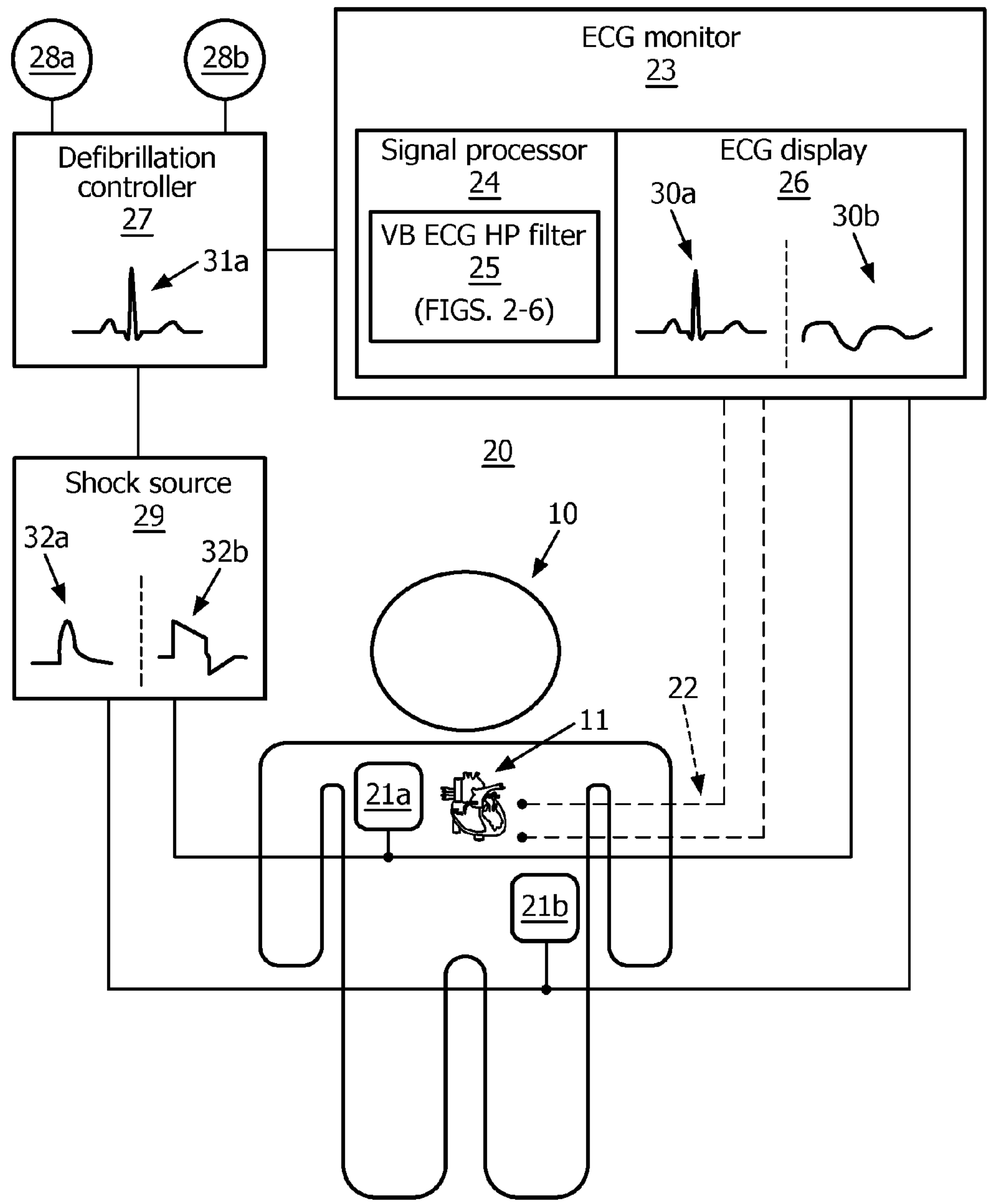
FIG. 1 illustrates an exemplary embodiment of a defibrillator with a ECG high pass filter in accordance with the present invention.

Referring to FIG. 1, a defibrillator 20 of the present invention employs a pair of electrode pads or paddles 21*a* and 21*b* (collectively hereafter as electrode pad/paddles 21), optional ECG leads 22, a ECG monitor 23 (internal or external), a defibrillation controller 27. and a shock source 29.

Electrode pads/paddles 21 are structurally configured as known in the art to be conductively applied to a patient 10 in an anterior-apex arrangement as shown in FIG. 1 or in an anterior-posterior arrangement (not shown). Electrode pad/paddles 21 conduct a defibrillation shock from shock source 29 to a heart 11 of patient 10 and conduct an ECG signal (not shown) representative of electrical activity of heart 11 of patient 10 to ECG monitor 23. Alternatively or concurrently, ECG leads 22 are connected to patient 10 as known in the art to conduct the ECG signal to ECG monitor 23.

ECG monitor 23 is structurally configured as known in the art for processing the ECG signal to measure the electrical activity of heart 11 of patient 10 as an indication patient 10 is experiencing an organized heartbeat condition or an unorganized heartbeat condition. An example of the ECG signal indicating an organized heartbeat condition is an ECG waveform 30*a* that is representative of an organized contraction of the ventricles of heart 11 of patient 10 being capable of pumping blood. An example of the ECG signal indicating an unorganized heartbeat condition is an ECG waveform 30*b* that is representative of a ventricular fibrillation of heart 11 of patient 10.

To this end, ECG monitor 23 employs a signal processor 24 and a ECG display 26. For purposes of the present invention, signal processor 24 is broadly defined herein as any structurally arrangement of hardware, software, firmware and/or circuitry for executing functions required by ECG monitor 23 in processing the ECG signal. Generally, in operation, signal processor 24 is structurally configured to receive the ECG signal representative of the electrical activity of heart 11 of patient 10 in analog form from pads/paddles 21 and/or ECG leads 22, to condition as necessary and stream the ECG signal to defibrillation controller 27, and to generate the ECG waveform for display by ECG display 26. More particularly, in practice, signal processor 24 may implement analog-to-digital converters and various filters including a low pass filter having a corner frequency (e.g., ≥20 Hz) for filtering high frequency signals and a ECG high pass filter 25 of the present invention having a variable corner frequency (e.g., ≤2 Hz, particularly 1.5 Hz) for filtering low frequency signals like baseline wander/drift, particularly due to defibrillation events. As will be explained further with the description herein of FIGS. 2-6, a structural design of ECG high pass filter 25 is a computationally simple design for achieving real time diagnostic quality ECG with excellent rejection to baseline wander. ECG high pass filter 25 also has excellent rejection baseline drift following a defibrillation event, and achieves the above performance with only minimal time delay (e.g., 250 ms) making it very useable for real time monitoring of the ECG signal. Additionally, ECG high pass filter 25 eliminates the need for the clinician to choose between diagnostic quality ECG and monitor quality ECG in order to keep the signal visible on the display.

For purposes of the present invention, ECG display 26 is broadly defined herein as any device structurally configured for presenting ECG waveform 30 for viewing including, but not limited to, a computer display and a printer.

Still referring to FIG. 1, shock source 29 is structurally configured as known in the art to store electric energy for delivery of a defibrillation shock 32 via electrode pads/paddles 21 to heart 11 of patient 10 as controlled by defibrillation controller 27. In practice, defibrillation shock 32 may have any waveform as known in the art. Examples of such waveforms include, but are not limited to, a monophasic sinusoidal waveform (positive sine wave) 32*a* and a biphasic truncated waveform 32*b* as shown in FIG. 1.

In one embodiment, shock source 29 employs a high voltage capacitor bank (not shown) for storing a high voltage via a high voltage charger and a power supply upon a pressing of a charge button 28*a*. Shock source 29 further employs a switching/isolation circuit (not shown) for selectively applying a specific waveform of an electric energy charge from the high voltage capacitor bank to electrode pads/paddles 21 as controlled by defibrillation controller 27.

Defibrillation controller 27 is structurally configured as known in the art to execute a manual synchronized cardioversion via a shock button 28*b* or an automatic synchronized cardioversion. In practice, defibrillation controller 27 employs hardware/circuitry (e.g., processor(s), memory, etc.) for executing a manual or an automatic synchronized cardioversion installed as software/firmware within defibrillation controller 27. In one embodiment, the software/firmware detects a QRS 31*a* of ECG signal 30 as a basis for controlling shock source 29 in delivering defibrillation shock 32 to heart 11 of patient 10.

Referring to FIGS. 2-6, a structural design of ECG high pass filter 25 in terms of operational performance and filter embodiments for achieving the operational performance will now be described herein to facilitate an understanding of the present invention.

Figure 2A:
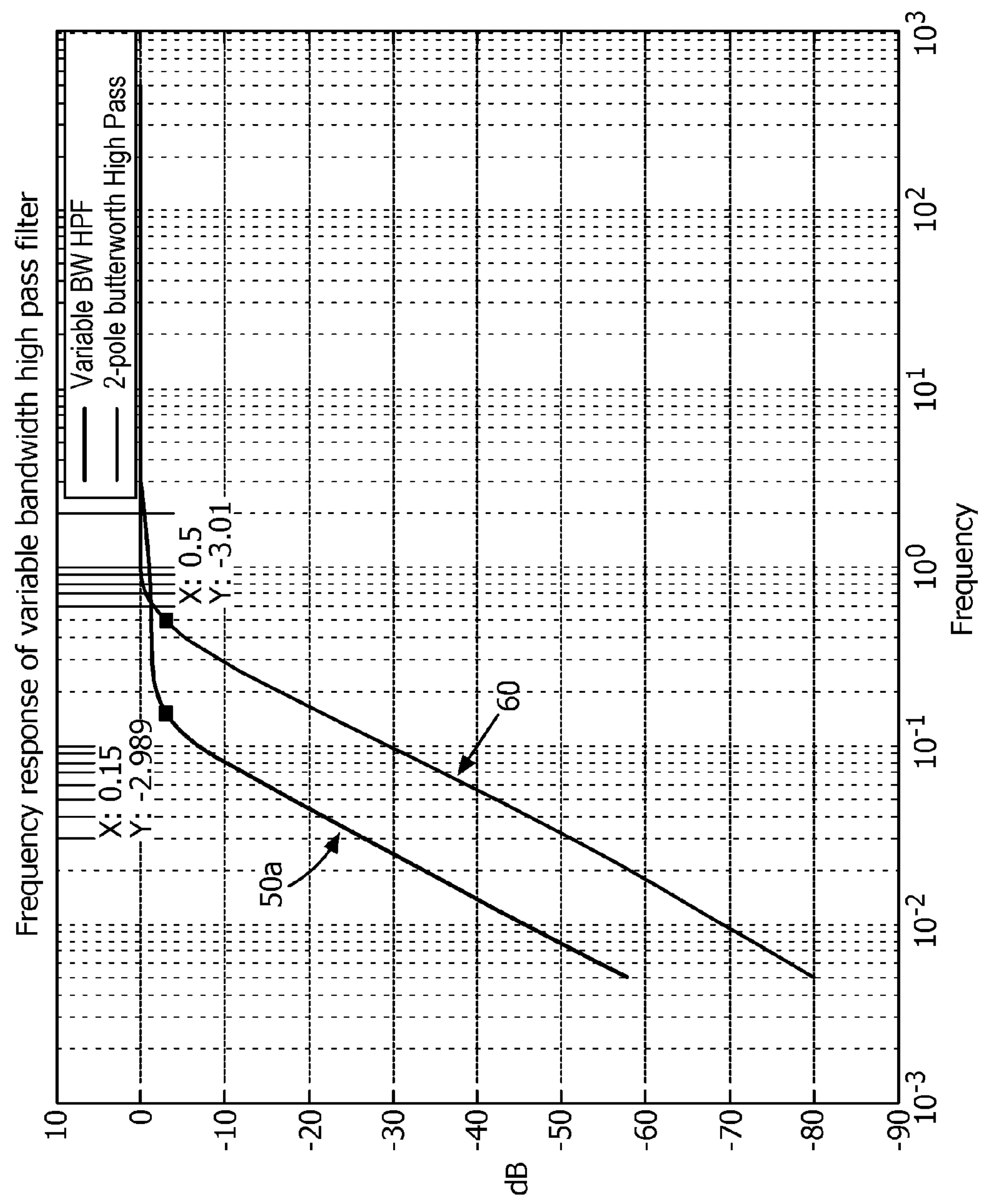
FIGS. 2A and 2B illustrate exemplary frequency responses of a ECG high pass filter of the present invention and a 2-pole Butterworth high pass filter as known in the art.
Figure 2B:
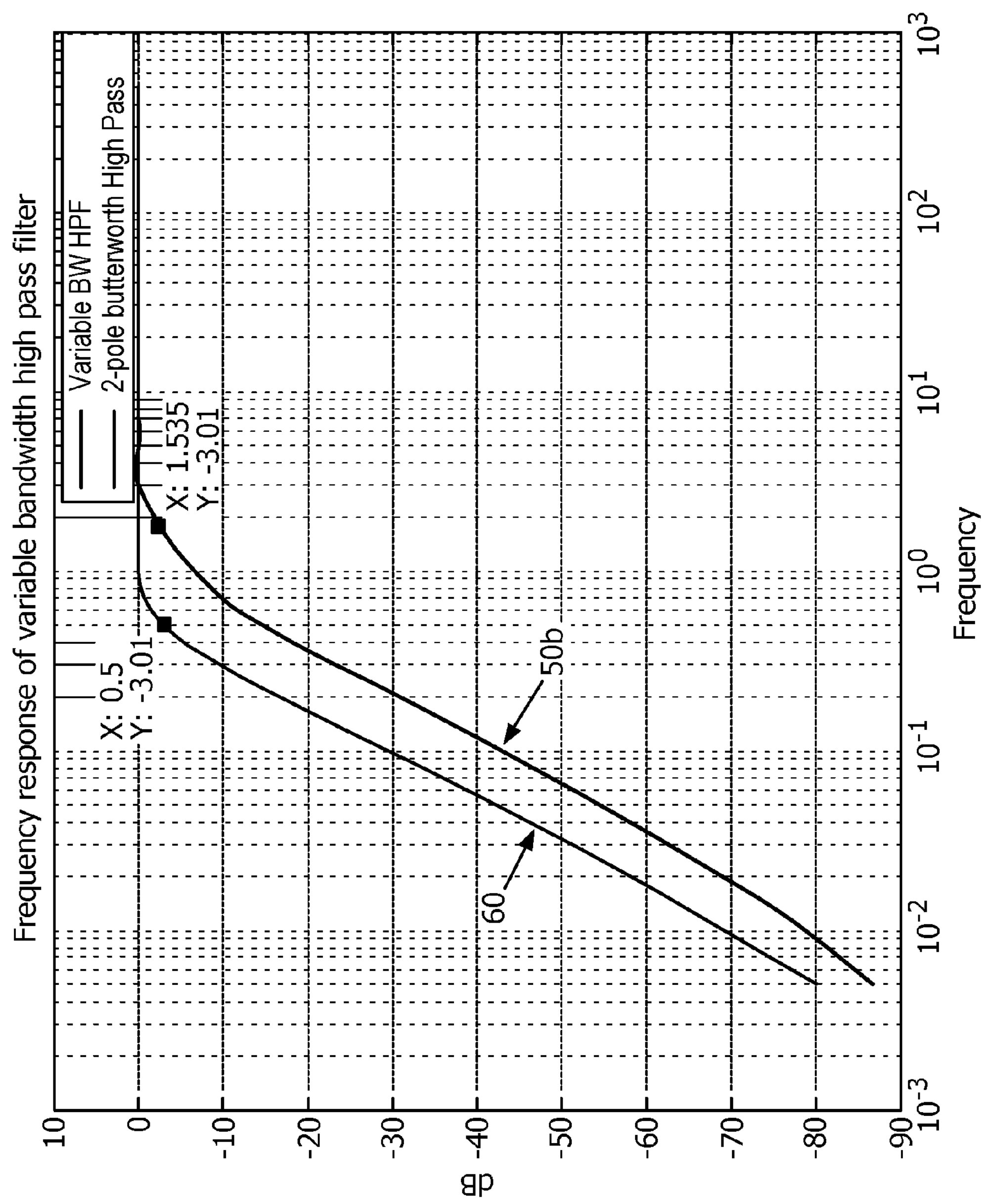
Figure 3A:
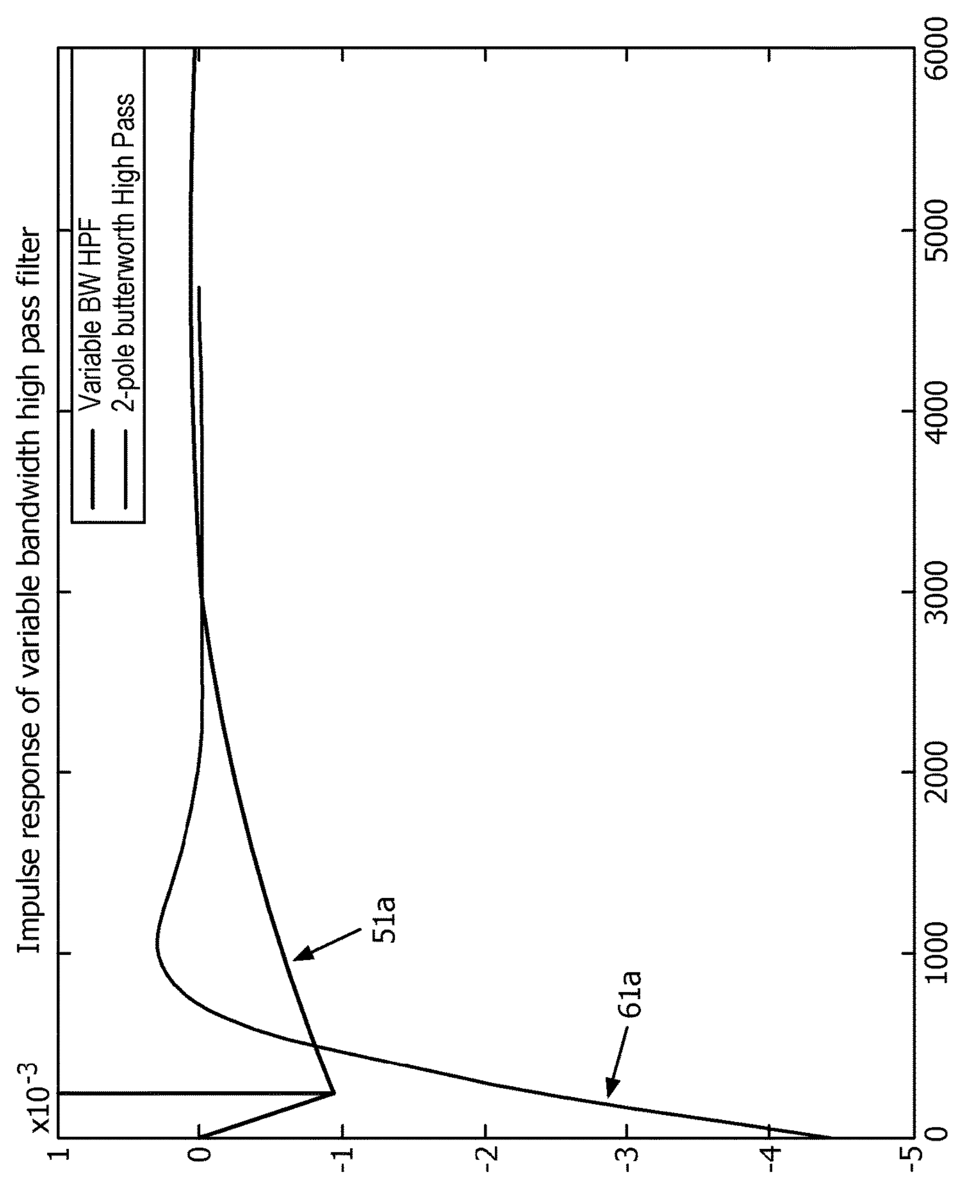
FIGS. 3A and 3B illustrate exemplary impulse responses of a ECG high pass filter of the present invention and a 2-pole Butterworth high pass filter as known in the art.
Figure 3B:
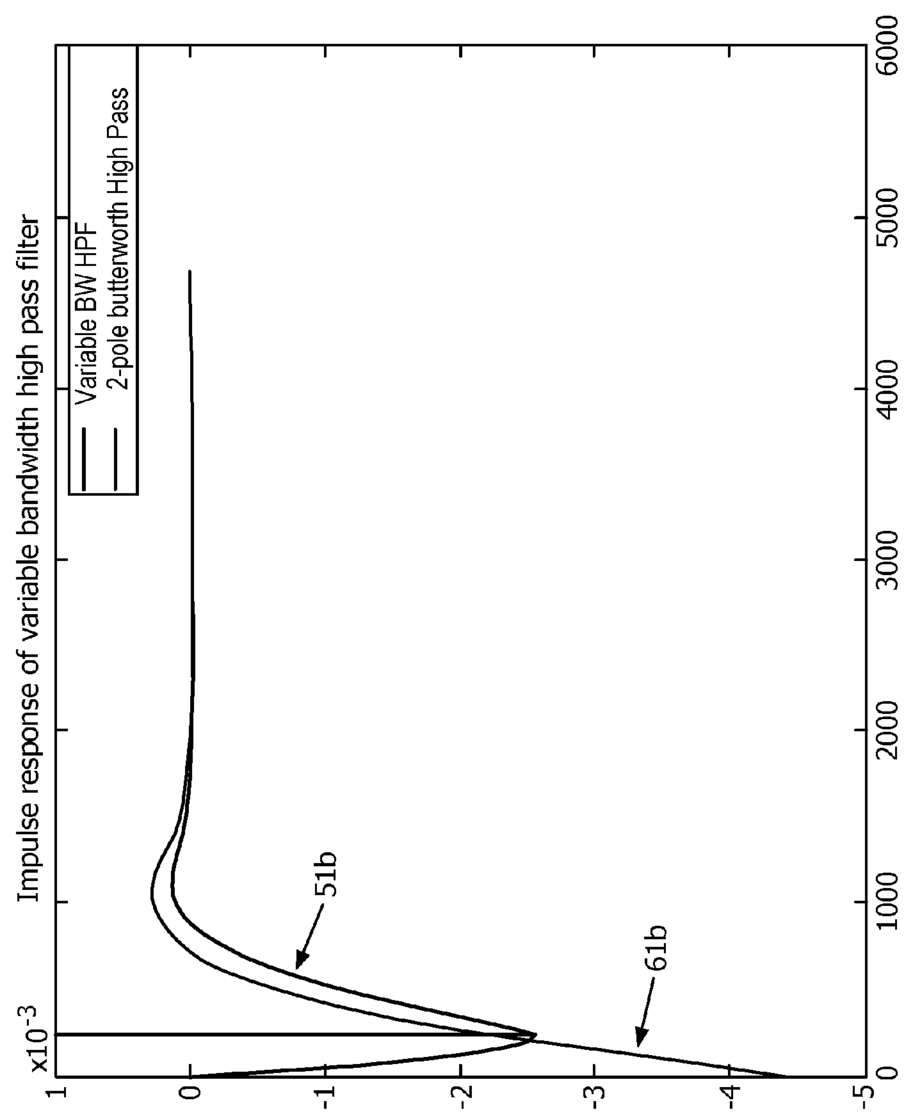

Specifically, as to the operational performance for diagnostic purposes, FIGS. 2 and 3 respectively provide an exemplary frequency response and an exemplary impulse response of ECG high pass filter 25 as compared to a known 2-pole Butterworth monitor bandwidth high pass filter (hereinafter "prior art ECG HP filter") with each filter having a second order frequency response and a sample rate of input ECG signal of 1000 Hz. As shown in FIGS. 2A and 2B, frequency responses 50*a* and 50*b* of ECG high pass filter 25 have a variable corner frequency ranging from 0.15 Hz to 1.535 Hz, respectively. Also shown is FIGS. 2A and 2B is a frequency response 60 of the prior art ECG HP filter having a 0.5 Hz corner frequency. As shown in FIGS. 3A and 3B, impulse response 51*a* and 51*b* of ECG high pass filter 25 have a value of baseline of the inputted ECG signal prior to the impulse at substantially the same level as the baseline after the impulse (i.e., an equivalent baseline before and after the impulse) while impulse responses 61*a* and 61*b* of the prior art ECG HP filter have a very large baseline shift following the impulse. FIG. 3A shows the impulse response of the variable high pass filter corner frequency set at 0.15 Hz. FIG. 3B shows the impulse response of the variable high pass filter corner frequency set at 1.535 Hz. Though not shown, the value of baseline of the inputted ECG signal prior to the impulse at substantially the same level as the baseline after the impulse over the full range of variable corner frequencies in between 0.15 Hz and 1.535 Hz.

Figure 4:
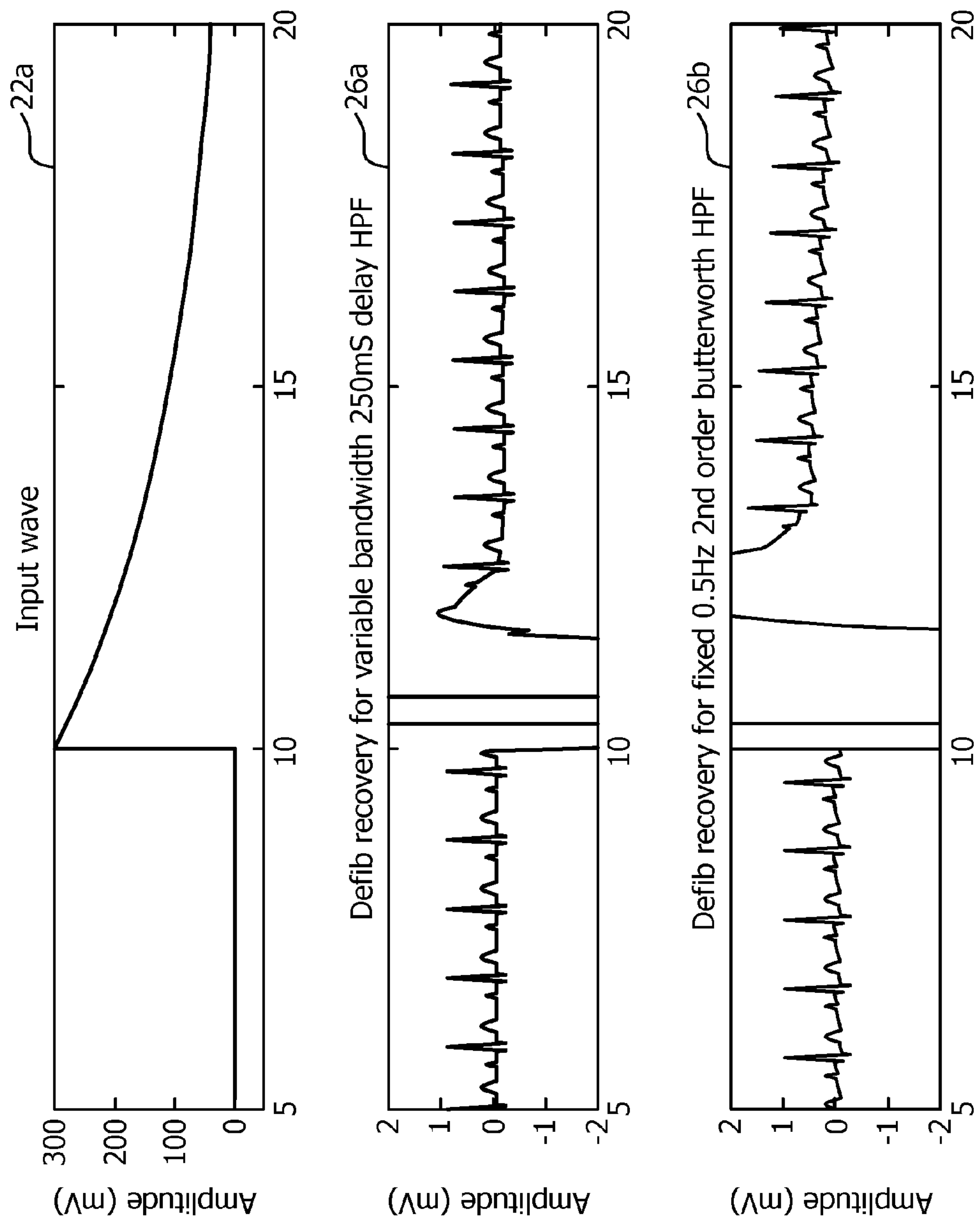
FIG. 4 illustrates exemplary defibrillation event recoveries of a ECG high pass filter of the present invention and a 2-pole Butterworth high pass filter as known in the art.

Also by example, FIG. 4 shows an input wave 22*a* of the ECG signal having a defibrillation event at time 10 s with an offset change of 300 mV and an exponential decay of five (5) second time constant. For this example, a defibrillation recovery 26*a* of ECG high pass filter 25 has a similar performance to a defibrillation recovery 26*b* of the prior art ECG HP filter.

Figure 5A:
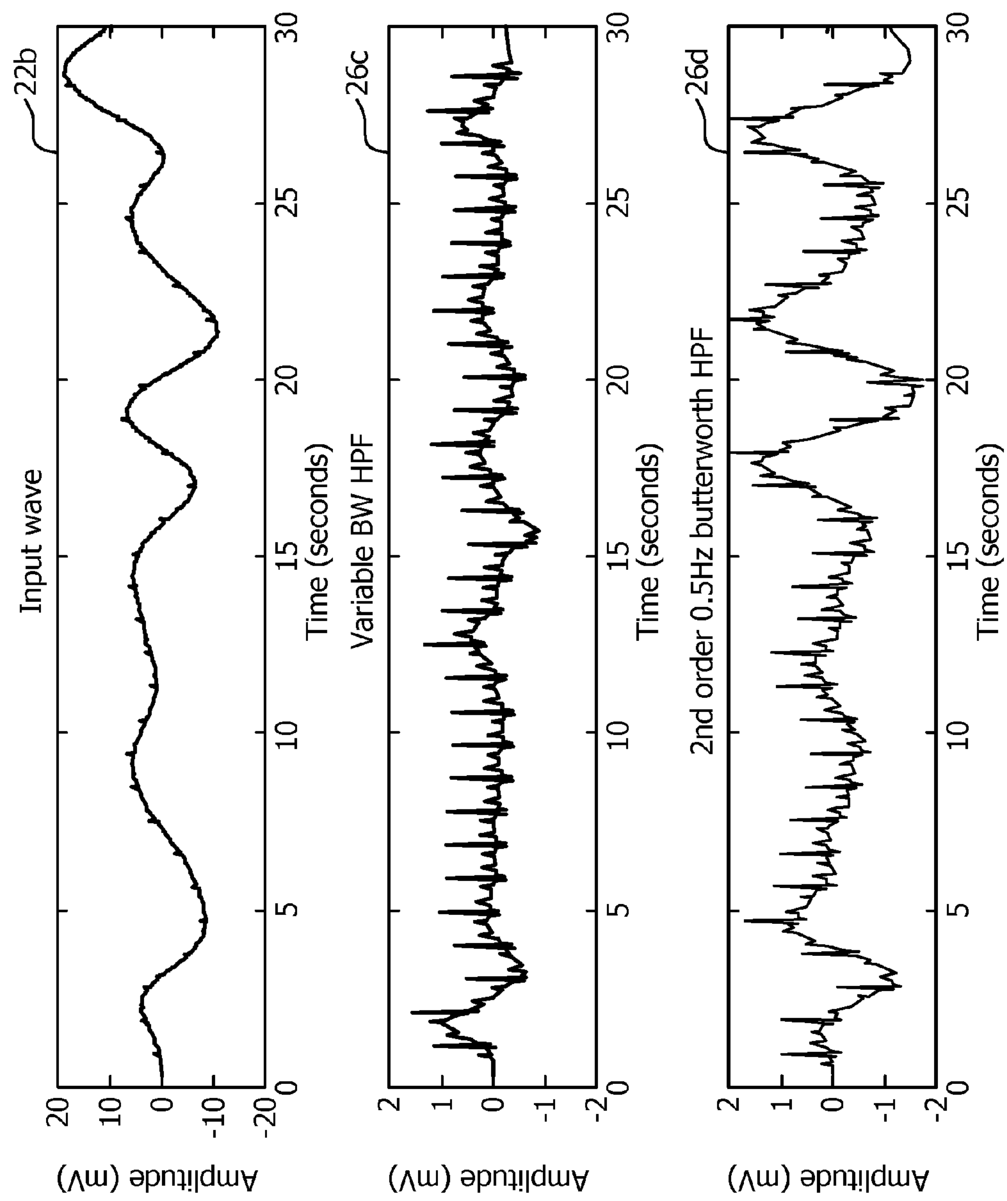
FIGS. 5A and 5B illustrate exemplary baseline wander responses of a ECG high pass filter of the present invention and a 2-pole Butterworth high pass filter as known in the art.

By further example, FIG. 5A shows a large level baseline wander 22*b* of the ECG signal. For this example, a center display 26*c* of the ECG signal as filtered by ECG high pass filter 25 has better performance and lower distortion of the ECG wave than a center display 26*d* of the ECG signal as filtered by the prior art ECG HP filter. More particularly, FIG. 5A shows a high level of baseline wander will result in a corner frequency for ECG high pass filter 25 being higher than the 0.5 Hz prior art ECG HP filter whereby the base line wander is maintained well within the display range (e.g., better than the 0.5 Hz filter) and even with the high corner frequency, the distortion of the ECG signal of ECG high pass filter 25 is less than the 0.5 Hz prior art ECG HP filter.

Figure 5B:
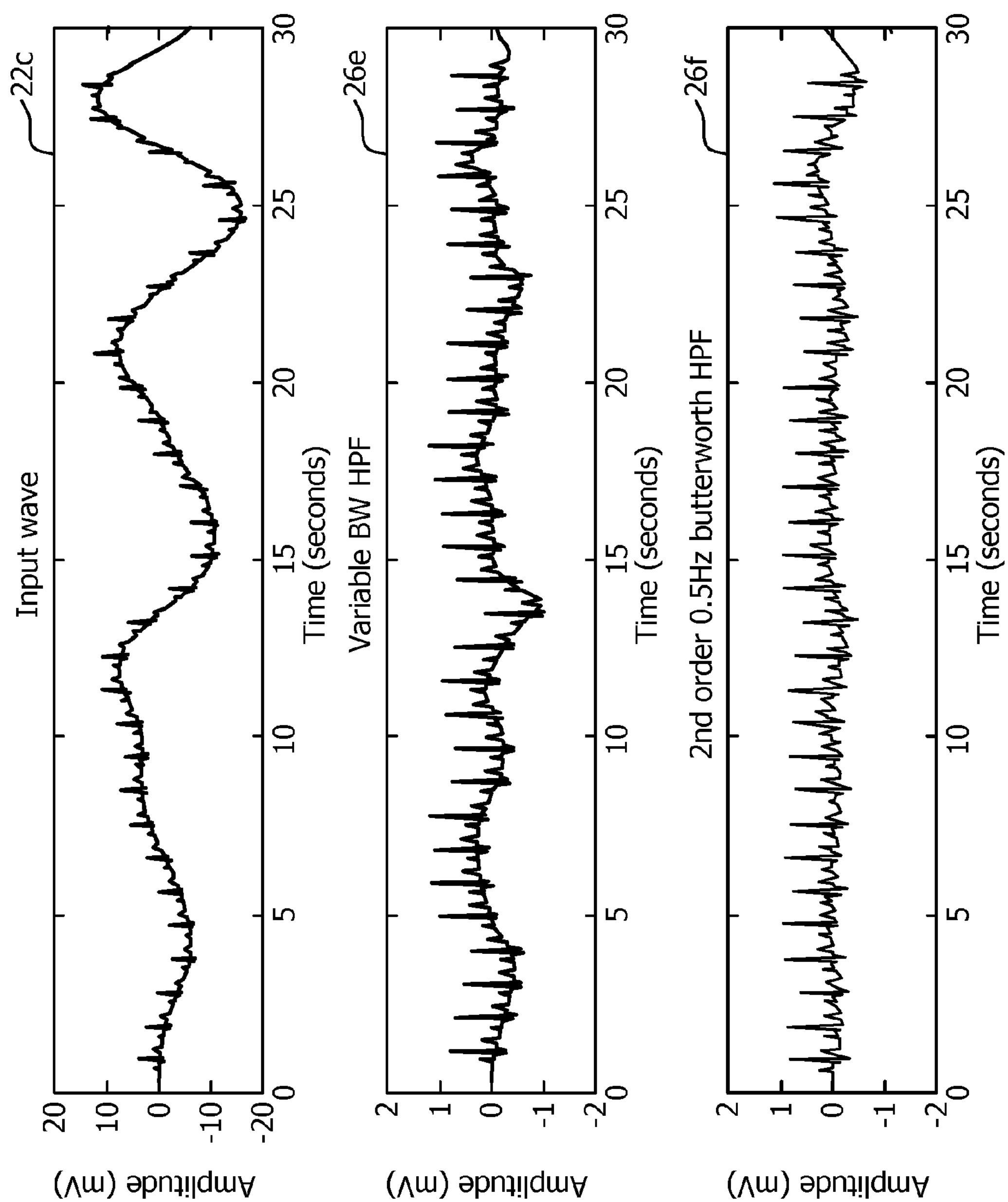

FIG. 5B shows a moderate level of baseline wander 22*c* of the ECG signal. For this example, a center display 26*e* of the ECG signal as filtered by ECG high pass filter 25 has minimal distortion of the ECG waveform while maintaining the ECG within the center display as compared to the center display and distortion of 26*f* of the ECG signal as filtered by the 0.5 Hz prior art ECG HP filter. More particularly, at a moderate level of baseline wander, the corner frequency of ECG high pass filter 25 will be lower than the of ECG high pass filter 25 yet the signal remains within the display range and the lower corner frequency of ECG high pass filter 25 minimizes the distortion of the ECG wave.

Figure 6A:
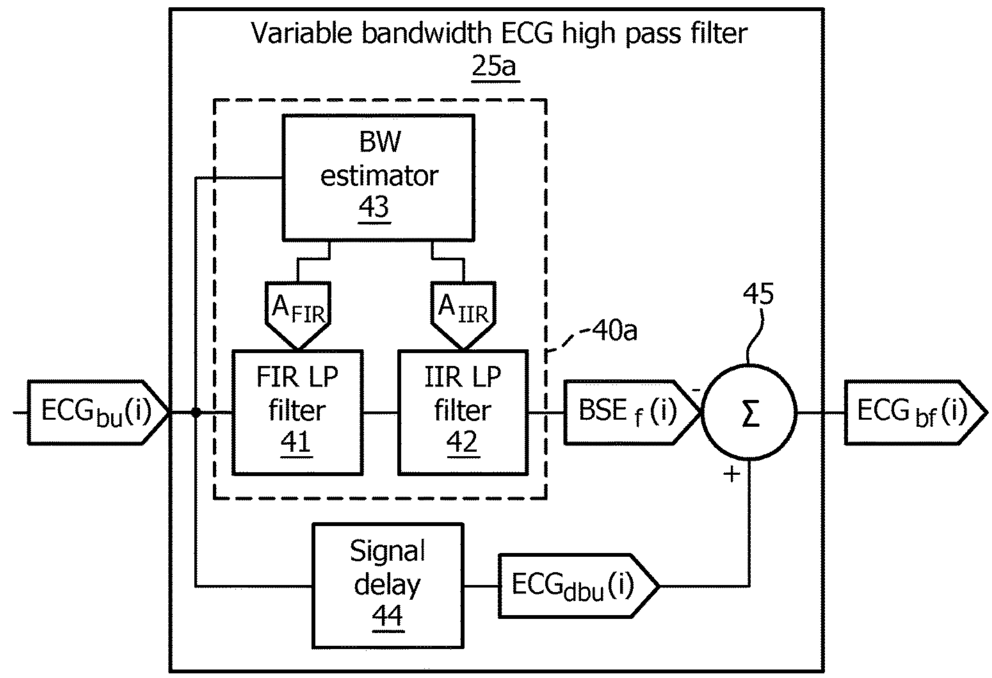
FIG. 6A illustrates a first exemplary embodiment of a ECG high pass filter in accordance with the present invention.
Figure 6B:
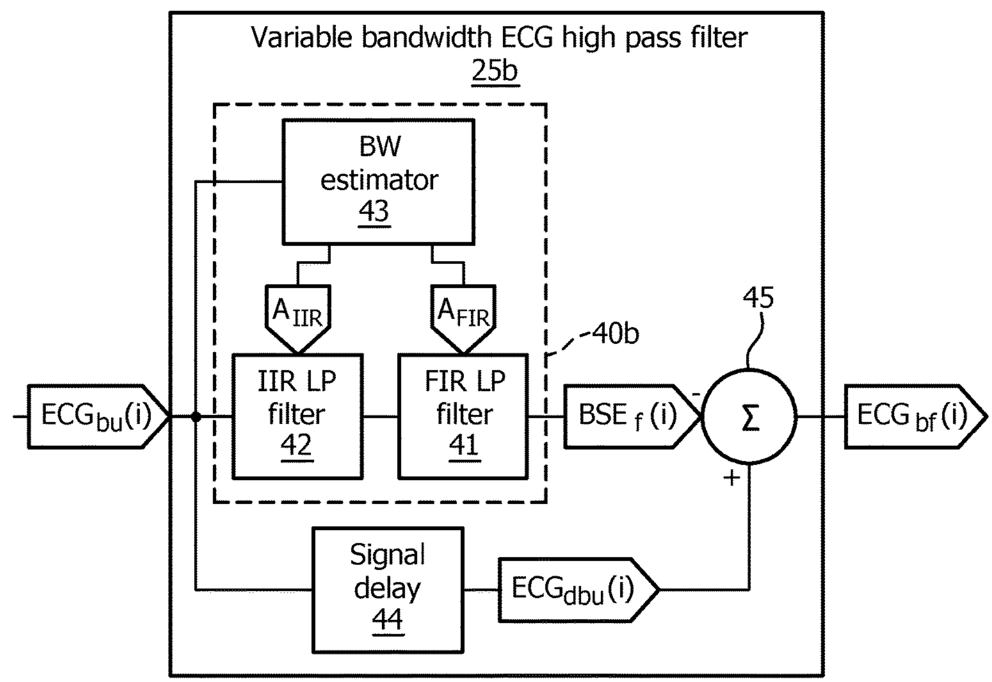
FIG. 6B illustrates a second exemplary embodiment of a ECG high pass filter in accordance with the present invention.

Referring to FIGS. 6A and 6B, structural embodiments of ECG high pass filter 25 for achieving such operational performance illustrated in FIGS. 2-5 include a baseline low pass filter 40 of the present invention, a signal delay 44 as known in the art and a signal extractor 45 as known in the art (e.g., an adder circuit). For embodiment 25*a* of ECG high pass filter 25, a baseline low pass filter 40*a* employs a series connection of FIR filter 41 and a IIR low pass filter 42 having coefficients dynamically adjusted by a baseline wander estimator 43 as shown in FIG. 6A. For embodiment 25*b* of ECG high pass filter 25, a baseline low pass filter 40*b* employs a series connection of IIR low pass filter 42 and FIR filter 41 having coefficients dynamically adjusted by a baseline wander estimator 43 as shown in FIG. 6B.

For both embodiments, ECG high pass filter 25 is operated as a filter having signal delay 44 for implementing as filter response as applied to a baseline unfiltered electrocardiogram signal $ECG_{bu}(i)$, which may have been previously low pass filtered for filtering high frequency signals (e.g., ≥20 Hz) and may have a predefined sample rate (e.g., a 1000 Hz). More importantly, baseline unfiltered electrocardiogram signal $ECG_{bu}(i)$ may include a baseline wander/drift. In operation, baseline unfiltered electrocardiogram signal $ECG_{bu}(i)$ is inputted into baseline low pass filter 40 and signal delay 44. A filtered baseline signal $BSE_f(i)$ representative of any baseline wander/draft is outputted by baseline low pass filter 40 and extracted by signal extractor 45 from a delayed baseline unfiltered electrocardiogram signal $ECG_{dbu}(i)$, which is delayed for real time ECG monitoring (e.g., 250 ms). The extraction yields a baseline filtered electrocardiogram signal $ECG_{bf}(i)$ exhibiting minimal distortion when baseline wander is minimal yet large baseline wander is effectively removed to keep the baseline filtered electrocardiogram signal $ECG_{bf}(i)$ on ECG display 26.

In practice, FIR filter 41 and IIR low pass filter 42 are cooperatively structurally designed for low pass filtering baseline unfiltered electrocardiogram signal $ECG_{bu}(i)$ whereby baseline filtered electrocardiogram signal $ECG_{bu}(i)$ is nonresponsive to a ramping of baseline unfiltered electrocardiogram signal $ECG_{bu}$(i) and/or a baseline shift due to a R-wave of $ECG_{bu}$(i) unfiltered electrocardiogram signal $ECG_{bu}$(i) is minimized.

In one embodiment of FIR filter 41, a boxcar FIR filter contains two (2) coefficients. Specifically, a current coefficient fir_coef(1) is at the current sample of the baseline unfiltered electrocardiogram signal $ECG_{bu}$(i) in accordance with the following equation [1] and a prior coefficient fir_coef(delay+1) is prior to the current sample of the baseline unfiltered electrocardiogram signal $ECG_{bu}$(i) at a time equivalent to the filter delay (e.g., 250 ms) in accordance with the following equation [2]:

$$\text{fir\_coef}(1)=0.9/FC\_LPF \quad [1]$$

$$\text{fir\_coef}(\text{delay}+1)=1-(0.9/FC\_LPF) \quad [2]$$

where FC_LPF is the 3 db corner frequency of IIR LP filter 42 in Hz.

In one embodiment of IIR low pass filter 42, a Butterworth $2^{nd}$ order low pass filter is utilized whereby Butterworth $2^{nd}$ order low pass filter has a z-transform H(z) that may written in accordance with the following equation [3]:

$$H(z)=\frac{b_0+b_1z^{-1}+b_2z^{-2}}{1+a_1z^{-1}+a_2z^{-2}} \quad [3]$$

An exemplary implementation of the Butterworth $2^{nd}$ order low pass filter for baseline low pass filter 40*a* (FIG. 6A) is in accordance with the following equation [4]:

$$y[i]=b_0w[i]+b_1w[i-1]+b_2w[i-2]-a_1y[i-1]-a_2y[i-2] \quad [4]$$

where y is filtered baseline signal $BSE_f$, w is the output of FIR filter 41, and a and b are coefficients of the Butterworth $2^{nd}$ order low pass filter for setting a corner frequency of the Butterworth $2^{nd}$ order low pass filter.

An exemplary implementation of the Butterworth $2^{nd}$ order low pass filter for baseline low pass filter 40*b* (FIG. 6B) is in accordance with the following equation [5]:

$$y[i]=b_0x[i]+b_1x[i-1]+b_2x[i-2]-a_1y[i-1]-a_2y[i-2] \quad [5]$$

where y is the output of the Butterworth $2^{nd}$ order low pass filter, x is baseline unfiltered electrocardiogram signal $ECG_{bu}$, and a and b are coefficients of the Butterworth $2^{nd}$ order low pass filter for setting a corner frequency of the Butterworth $2^{nd}$ order low pass filter.

In practice, baseline wander estimator 43 estimates the level of baseline wander of baseline unfiltered electrocardiogram signal $ECG_{bu}$ as known in the art and dynamically adjusts the coefficients of FIR filter 41 and IRR LP filter 42 by appropriate increasing or decreasing the corner frequency of IRR LP filter 42 dependent upon the estimated level of baseline wander of baseline unfiltered electrocardiogram signal $ECG_{bu}$.

In one embodiment, baseline wander estimator 43 dynamically adjusts coefficients of FIR filter 41 and IIR LP filter 42 in dependence of the estimated level of baseline wander of baseline unfiltered electrocardiogram signal $ECG_{bu}$ and outputs adjustment signals $A_{FIR}$ and $A_{IIR}$ respectively consisting of dynamically adjusted coefficients of FIR filter 41 and IIR LP filter 42.

In an alternative embodiment, baseline wander estimator 43 dynamically adjusts a corner frequency $CF_{IIR}$ of IIR LP filter 42 in dependence of the estimated level of baseline wander of baseline unfiltered electrocardiogram signal $ECG_{bu}$ and outputs the outputs adjustment signals $A_{FIR}$ and $A_{IIR}$ consisting of the dynamically adjusted corner frequency $CF_{IIR}$ whereby FIR filter 41 and IIR LP filter 42 dynamically adjusts respective coefficients.

Referring to FIGS. 1-6, those having ordinary skill in the art will appreciate numerous benefits of the present invention including, but not limited to, (1) substantial reduction in the computational requirement for implementing a ECG high pass filter that minimally distorts the ECG signal and has an excellent rejection of baseline wander/drift, particularly following a defibrillation event and (2) a ECG high pass filter configurable for both diagnostic purposes and EMS purposes.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A variable bandwidth electrocardiogram high pass filter comprising:

a baseline low pass filter including a series connection of a boxcar finite impulse response low pass filter and a Butterworth $2^{nd}$ order infinite impulse response low pass filter for low pass filtering a baseline unfiltered electrocardiogram signal ($ECG_{bu}$) to output a filtered baseline signal ($BSE_f$), wherein the baseline low pass filter further includes a baseline wander estimator operably connected to at least one of the boxcar finite impulse response low pass filter and the Butterworth $2^{nd}$ order infinite impulse response low pass filter for dynamically adjusting a corner frequency of the baseline low pass filter as a function of an estimation of any baseline wander within the baseline unfiltered electrocardiogram signal ($ECG_{bu}$);

a signal delay for time delaying the baseline unfiltered electrocardiogram signal ($ECG_{bu}$) to output a delayed baseline unfiltered electrocardiogram signal ($ECGd_{bu}$); and a signal extractor connected to the baseline low pass filter and the signal delay for extracting the filtered baseline signal ($BSE_f$) from the delayed baseline unfiltered electrocardiogram signal ($ECGd_{bu}$) to output a baseline filtered electrocardiogram signal ($ECG_{bf}$).

2. The variable bandwidth electrocardiogram high pass filter of claim 1, wherein the boxcar finite impulse response low pass filter includes a plurality of coefficients;

wherein the Butterworth $2^{nd}$ order infinite impulse response low pass filter has a corner frequency; and wherein the series connection of the boxcar finite impulse response low pass filter and the Butterworth $2^{nd}$ order infinite impulse response low pass filter outputs the baseline filtered electrocardiogram signal ($ECG_{bf}$) being nonresponsive to a ramping of the baseline unfiltered electrocardiogram signal ($ECG_{bu}$) as a function of a ratio of a current sample coefficient of the boxcar finite impulse response low pass filter to an inverse of the corner frequency of the Butterworth $2^{nd}$ order infinite impulse response low pass filter.

3. The variable bandwidth electrocardiogram high pass filter of claim 2, wherein the corner frequency of the Butterworth $2^{nd}$ order infinite impulse response low pass filter is a function of the estimation of any baseline wander within the baseline unfiltered electrocardiogram signal ($ECG_{bu}$).

4. The variable bandwidth electrocardiogram high pass filter of claim 2, wherein a prior sample coefficient of the boxcar finite impulse response low pass filter is a constant minus the current sample coefficient.

5. The electrocardiogram high pass filter of claim 1, wherein the series connection of the boxcar finite impulse response low pass filter and the Butterworth $2^{nd}$ order infinite impulse response low pass filter includes a gain of the baseline low pass filter being equal to a gain of the signal delay.

6. An electrocardiogram monitor, comprising:

a signal processor operable to generate an electrocardiogram waveform of a heart of a patient, wherein the signal processor includes a baseline low pass filter including a series connection of a boxcar finite impulse response low pass filter and a Butterworth $2^{nd}$ order infinite impulse response low pass filter cooperatively for low pass filtering a baseline unfiltered electrocardiogram signal ($ECG_{bu}$) to output a filtered baseline signal ($BSE_f$), wherein the baseline low pass filter further includes a baseline wander estimator connected to at least one of the finite impulse response filter and the infinite impulse response low pass filter, for dynamically adjusting a corner frequency of the baseline low pass filter as a function of an estimation of any baseline wander within the baseline unfiltered electrocardiogram signal ($ECG_{bu}$), a signal delay for time delaying the baseline unfiltered electrocardiogram signal ($ECG_{bu}$) to output a delayed baseline unfiltered electrocardiogram signal ($ECGd_{bu}$), and a signal extractor connected to the baseline low pass filter and the signal delay for extracting the filtered baseline signal ($BSE_f$) from the delayed baseline unfiltered electrocardiogram signal ($ECGd_{bu}$) to output a baseline filtered electrocardiogram signal ($ECG_{bf}$); and an electrocardiogram display operably connected to the signal processor to display the electrocardiogram waveform.

7. The electrocardiogram monitor of claim 6, wherein the boxcar finite impulse response low pass filter includes a plurality of coefficients;

wherein the Butterworth $2^{nd}$ order infinite impulse response low pass filter has a corner frequency; and wherein the series connection of the boxcar finite impulse response low pass filter and the Butterworth $2^{nd}$ order infinite impulse response low pass filter outputs the baseline filtered electrocardiogram signal ($ECG_{bf}$) being nonresponsive to a ramping of the baseline unfiltered electrocardiogram signal ($ECG_{bu}$) as a function of a ratio of a current sample coefficient of the boxcar finite impulse response low pass filter to an inverse of a corner frequency of the Butterworth $2^{nd}$ order infinite impulse response low pass filter.

8. The electrocardiogram monitor of claim 7, wherein the corner frequency of the Butterworth $2^{nd}$ order infinite impulse response low pass filter is a function of a corner frequency of the estimation of any baseline wander within the baseline unfiltered electrocardiogram signal ($ECG_{bu}$).

9. The electrocardiogram monitor of claim 7, wherein a prior sample coefficient of the boxcar finite impulse response low pass filter is a constant minus the current sample coefficient.

10. The electrocardiogram monitor of claim 6, wherein the series connection of the boxcar finite impulse response low pass filter and the Butterworth $2^{nd}$ order infinite impulse response low pass filter includes a gain of the baseline low pass filter being equal to a gain of the signal delay.

11. A defibrillator, comprising:

an electrocardiogram monitor operable to generate an electrocardiogram waveform of a heart of a patient, wherein the electrocardiogram monitor includes a baseline low pass filter including a series connection of a boxcar finite impulse response low pass filter and a Butterworth $2^{nd}$ order infinite impulse response low pass filter for low pass filtering a baseline unfiltered electrocardiogram signal ($ECG_{bu}$) to output a filtered baseline signal ($BSE_f$), wherein the baseline low pass filter further includes a baseline wander estimator connected to at least one of the finite impulse response filter and the infinite impulse response low pass filter for dynamically adjusting a corner frequency of the baseline low pass filter as a function of an estimation of any baseline wander within the baseline unfiltered electrocardiogram signal ($ECG_{bu}$), a signal delay for time delaying the baseline unfiltered electrocardiogram signal ($ECG_{bu}$) to output a delayed baseline unfiltered electrocardiogram signal ($ECGd_{bu}$), and a signal extractor connected to the baseline low pass filter and the signal delay for extracting the filtered baseline signal ($BSE_f$) from the delayed baseline unfiltered electrocardiogram signal ($ECGd_{bu}$) to output a baseline filtered electrocardiogram signal ($ECG_{bf}$);

a shock source operable to store shock energy; and a defibrillation controller operably connected to the electrocardiogram monitor and the shock source to control a delivery of the shock energy to the hearth of the patient responsive to a QRS analysis of the electrocardiogram waveform.

12. The defibrillator of claim 11, wherein the boxcar finite impulse response low pass filter includes a plurality of coefficients;

wherein the Butterworth $2^{nd}$ order infinite impulse response low pass filter has a corner frequency; and wherein the series connection of the boxcar finite impulse response low pass filter and the Butterworth $2^{nd}$ order infinite impulse response low pass filter outputs the baseline filtered electrocardiogram signal ($ECG_{bf}$) being nonresponsive to a ramping of the baseline unfiltered electrocardiogram signal ($ECG_{bu}$) as a function of a ratio of a current sample coefficient of the boxcar finite impulse response low pass filter to an inverse of a corner frequency of the Butterworth $2^{nd}$ order infinite impulse response low pass filter.

13. The defibrillator of claim 12, wherein the corner frequency of the Butterworth $2^{nd}$ order infinite impulse response low pass filter is a function of a corner frequency of the estimation of any baseline wander within the baseline unfiltered electrocardiogram signal ($ECG_{bu}$).

14. The defibrillator of claim 12, wherein a prior sample coefficient of the boxcar finite impulse response low pass filter is a constant minus the current sample coefficient.

15. The defibrillator of claim 11, wherein the series connection of the boxcar finite impulse response low pass filter and the Butterworth $2^{nd}$ order infinite impulse response low pass filter includes a gain of the baseline low pass filter being equal to a gain of the signal delay.

* * * * *